United States Patent [19]

Warriner

[11] Patent Number: Plant 6,083

[45] Date of Patent: Jan. 19, 1988

[54] ROSE PLANT JACTRED

[75] Inventor: William A. Warriner, Tustin, Calif.

[73] Assignee: Jackson & Perkins Company, Medford, Oreg.

[21] Appl. No.: 825,362

[22] Filed: Feb. 3, 1986

[51] Int. Cl.[4] ..... A01H 5/00

[52] U.S. Cl. ..... Plt./20

[58] Field of Search ..... Plt. 20

*Primary Examiner*—James R. Feyrer

*Attorney, Agent, or Firm*—Manford R. Haxton

[57] ABSTRACT

A hybrid tea rose variety having continuous production of large red flowers, upright and vigorously growing bush, 7 leaflet leaves and bright yellow anthers with red centers.

1 Drawing Figure

This present invention relates to a new and distinct variety of rose plant of the hybrid tea class which was originated by crossing an unnamed variety with the variety American Pride, U.S. Plant Pat. No. 4,139.

The primary objective of this breeding was to produce a new rose variety of the hybrid tea class with large red blossoms, excellent vigor and full season flower production. This objective was substantially achieved along with other desirable improvements as evidenced by the following unique combination of characteristics which are outstanding in the new variety and which distinguish it from its parents as well as from all other varieties of which I am aware:

1. Large (5") bright red flowers;
2. Vigorous upright growing bush;
3. Heavy and continuous flower production;
4. Frequent 7 leaflet leaves;
5. A slight flower fragrance; and
6. Anthers of bright yellow with reddish centers.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—American Pride, U.S. Plant Pat. No. 4,139.

Classification:

*Botanical.*—Rosa hybrid.

*Commercial.*—Hybrid tea.

FLOWER

Observations made from specimens grown in a greenhouse at Irvine, Calif. in September, 1985.

Blooming habit: Continuous.

Bud:

*Size.*—1½" when petals start to unfurl.

*Form.*—Long, pointed.

*Color.*—When sepals first divide, dark red, Red Group 46A; when half blown, upper side of petals bright red, Red Group 45A to B; lower side of petals Red Group 53B to C.

*Sepals.*—Color: Green Group 143B to 143C. Three appendaged sepals normally appendaged. Two unappendaged sepals, smooth to very fine hairy edge.

*Receptacle.*—Color: Green Group 143A. Shape: Funnel. Size: Medium. Surface: Smooth.

*Peduncle.*—Length: Medium. Surface: Prickly and glandular. Color: Bronzy. Strength: Stiff.

Open bloom:

*Size.*—Large. Average open size 5".

*Borne.*—Singly to several together.

*Stems.*—Medium.

*Form.*—When first open, high center. Permanence: Retains its form to the end.

*Petalage.*—Number of petals under normal conditions: 30.

*Color.*—Center of flower: Upper side of petals, Red Group 45A to B; reverse side of petals, Red Group 53B to C. Base of petals, small cream colored circle. Major color: Red Group 45A to B.

*Variegations.*—Occasional white streak on outside petals.

*Discoloration.*—General tonality at end of first day: None. Third day: Some fading.

*Fragrance.*—Slight.

Petals:

*Texture.*—Thick.

*Shape.*—Obovate.

*Form.*—Tips slightly recurved.

*Arrangement.*—Imbricated.

*Persistence.*—Drop off cleanly.

*Lastingness.*—On the plant, long. As cut flowers, long.

Reproductive parts:

*Anthers.*—Medium. Color: Yellow and reddish near the center of each anther. Arrangement: Regular around styles.

*Filaments.*—Color: Reddish.

*Pollen.*—Lemon yellow.

*Styles.*—Color: Red.

*Stigmas.*—Color: Reddish white.

PLANT

Form: Bush.
Growth: Vigorous.
Foliage:
*Number of leaflets on normal mid-stem leaves.*—5 to 7.
*Size.*—Large.
*Quantity.*—Normal.
*Color.*—New foliage: Reddish. Old foliage: Medium green (Green Group 137A).
Leaflets:
*Shape.*—Oval pointed.
*Texture.*—Smooth.
*Edge.*—Serrated.
*Serration.*—Single.
*Petiole.*—Rachis: Color: Green. Underside: Smooth, with prickles.
*Stipules.*—Medium, bearded.
*Disease resistance.*—Susceptible to mildew, under normal growing conditions at Irvine, Calif.

Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Medium, hooked downward.
*Color when young.*—Red.
Small prickles:
*Quantity.*—On main stalks, few to none. On laterals, few.
*Color.*—Brown.

I claim:

1. A new and distinct variety of rose plant of the hybrid tea class, substantially as herein shown and described, characterized particularly as to novelty by the unique combination of its continuous production of large red flowers, its upright and vigorously growing bush, its 7 leaflet leaves and its bright yellow anthers with red centers.

* * * * *

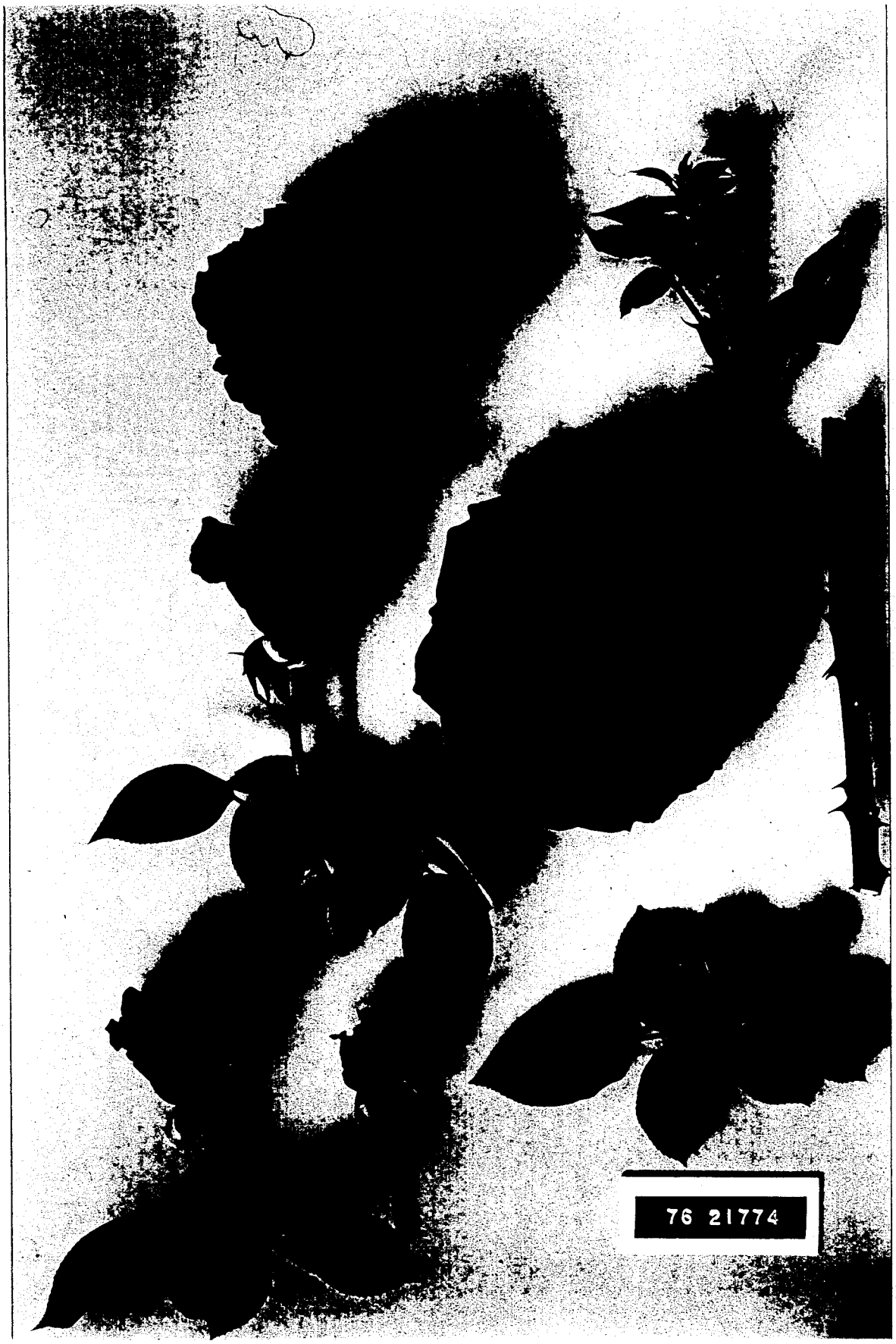
76 21774